US007705011B2

(12) United States Patent
Igarashi et al.

(10) Patent No.: US 7,705,011 B2
(45) Date of Patent: Apr. 27, 2010

(54) AGENT FOR TREATMENT AND PREVENTION OF ENDOMETRIOSOS AND UTERINE ADENOMYOSIS

(76) Inventors: Masao Igarashi, 4-42-7, Hiyoshi-Cho, Maebashi-Shi, Gunma-Ken (JP); Toshio Igarashi, B205, Yushudai-Shukusha, 1-7-1, Yushudai-Higashi, Ichihara-Shi, Chiba-Ken (JP); Shigeo Igarashi, 535-8, Shimohosoi-Cho, Maebashi-Shi, Gunma-Ken (JP)

( * ) Notice: Subject to any disclaimer, the term of this patent is extended or adjusted under 35 U.S.C. 154(b) by 8 days.

(21) Appl. No.: 11/886,234

(22) PCT Filed: Mar. 15, 2006

(86) PCT No.: PCT/JP2006/305136

§ 371 (c)(1),
(2), (4) Date: Sep. 13, 2007

(87) PCT Pub. No.: WO2006/098371

PCT Pub. Date: Sep. 21, 2006

(65) Prior Publication Data

US 2008/0182830 A1 Jul. 31, 2008

(30) Foreign Application Priority Data

Mar. 16, 2005 (JP) .............................. 2005-075735

(51) Int. Cl.
*A61K 31/58* (2006.01)
*A61K 31/44* (2006.01)
*C07D 211/70* (2006.01)
*A61P 15/00* (2006.01)

(52) U.S. Cl. ........................ 514/277; 546/348; 514/176

(58) Field of Classification Search ........................ None
See application file for complete search history.

(56) References Cited

U.S. PATENT DOCUMENTS

| 4,757,076 A * | 7/1988 | Hirsch et al. ................. 514/277 |
| 2003/0064989 A1 * | 4/2003 | Talbot et al. ................. 514/242 |
| 2004/0121968 A1 * | 6/2004 | Ljubimov et al. ............. 514/43 |

FOREIGN PATENT DOCUMENTS

| JP | 2000-505422 | 5/2000 |
| JP | 2005-053783 | 3/2005 |
| WO | 02/098853 | 12/2002 |

OTHER PUBLICATIONS

Merck Manual regarding "Endometriosis".*
Merck Manual regarding "Endometriosis", May 2007.*
Masao Igarashi et al., "*High CD44 content in ovarian endometriotic cysts*", Fertility and Sterility, vol. 80, No. 4, pp. 1065-1066 (2003).
Lin Ji et al., "*Identification of Pyridine Compounds in Cigarette Smoke Solution that Inhibit Growth of the Chick Chorioallantoic Membrane*", Toxicological Sciences 69, pp. 217-225 (2002).
G. Melkonian et al., "*CD44 and tenascin play critical roles in growth and vascular development of the chick chorioallantoic membrane and are targets of cigarette smoke*", Anat Embryol 208, pp. 109-120 (2004).
Fabio Parazzini et al., "*Risk Factors for adenomyosis*", Human Reproduction, vol. 12, No. 6, pp. 1275-1279 (1997).
Daniel W. Cramer et al., "*The Relation of Endometriosis to Menstrual Characteristics, Smoking, and Exercise*", JAMA, vol. 255, No. 14, pp. 1904-1908 (1986).
Craig A. Witz et al., "*Pathogenesis of endometriosis—current research*", Human Fertility 6, pp. 34-40 (2003).
P.G. Groothuis et al., "*Inhibition of Endometrial Peritoneal Attachment in the Prevention and Treatment of Endometriosis*", Gynecol Obstet Invest 57, pp. 52-53 (2004).
Deborah J. Harrington et al., "*Tenascin is Differentially Expressed in Endometrium and Endometriosis*", Journal of Pathology 187, pp. 242-248 (1999).
Stephen L. Corson, Endometriosis, The Enigmatic Disease, pp. 6-7 (1992).
Janice Rymer, et al., Gynaecology, pp. 57-58 (1997).
I. C. Rubin & Josef Novak, Integrated Gynecology, Principles and Practice, p. 115 (1956).
Allan Templeton, et al., Evidence-based Fertility Treatment, p. 246 (1998).
Phyllis L. Carr, et al., The Medical Care of Women, p. 67 (1996).
Robert W. Kistner, Gynecology Principles and Practice, p. 361(1986).
Charles R. B. Beckmann, Obstetric & Gynecology, p. 397 (2002).
Ralph C. Benson, current Obstetric & Gynecologic Diagnosis & Treatment, p. 395 (1982).
John A. Rock & John D. Thompson, TE LINDE'S Operative Gynecology, xxii contents (1997).
Claude Gompel, M.D. et al., Pathology in Gynecology and Obstetric, p. 425 (1994).
Robert W. Shaw, et al., Gynaecology, p. 457 (1997).
Camran R. Nezhat, et al., Endometriosis Advanced Management and Surgical Techniques, p. 229 (1995).
Masato Nishida, et al., Gynecol Obstet Invest, 2000; 50(suppl 1): 18-25.
Louise A. Brinton, et al., Am J Obstet Gynecol 1997; 176:572-3.
Sutton C. et al: Modern Management of Endometriosis. Taylor & Francis, pp. 17-19, (2006).
Sutton C. et al: Modern Management of Endometriosis. Taylor & Francis, p. 25, (2006).

(Continued)

*Primary Examiner*—Brian-Yong S Kwon
*Assistant Examiner*—Bong-Sook Baek
(74) *Attorney, Agent, or Firm*—Wenderoth, Lind & Ponack, LLP.

(57) ABSTRACT

An object of the present invention is to provide an agent for use in the effective treatment and prevention of endometriosis and uterine adenomyosis. The present invention relates to an agent for use in the treatment and prevention of endometriosis or uterine adenomyosis, comprising, as an active ingredient, a compound selected from the group consisting of 3-ethylpyridine, 3-methylpyridine, 2-ethylpyridine, and 2-methylpyridine.

9 Claims, No Drawings

OTHER PUBLICATIONS

Igarashi M. et al: A novel therapeutic agent for the treatment of endometriosis: 3-ethyl pyridine. Direct effects of a 3-ethyl pyridine-loaded vaginal ring on deep and vaginal endometriosis. Abstract of 9th World Congress on Endometriosis,2005. European J of Obstet Gynecol and Reproductive Biology 123: Suppl. 1, S59, (2005).

Igarashi TM et al. A novel therapeutic agent for the treatment of endometriosis: 3-ethyl pyridine (3EP), detected from tobacco smoke. Direct effects of a 3EP-loaded vaginal ring on deep and vaginal endometriosis. Fertil Steril 88: Suppl.1. S252, (2007).

Igarashi TM et al. A novel anti-endometriosis agent; 3-ethyl pyridine(3EP), detected from tobacco smoke. Direct effects of a 3EP-loaded vaginal ring on deep or vaginal endometriosis. Abstract & Program Book of 10th World Congress on Endometriosis. p. 57, (2008).

Jonathan S. Berek, Novak's Gynecology, 13$^{th}$ Ed., pp. 1271-1275, 1220-1221 and 1176-1177, (2002).

Pub Med Search Results (2009).

Supplementary European Search Report for corresponding European Application No. 06 72 9157 (Jan. 13, 2009).

* cited by examiner

AGENT FOR TREATMENT AND PREVENTION OF ENDOMETRIOSOS AND UTERINE ADENOMYOSIS

FIELD OF THE INVENTION

The present invention relates to an agent for use in the treatment and prevention of endometriosis and uterine adenomyosis, which comprising 3-ethylpyridine as an active ingredient.

BACKGROUND ART

The number of women suffering from infertility or menstrual pain due to endometriosis or uterine adenomyosis has been increasing.

Current therapeutic agents for endometriosis include danazol and GnRH analogs. The agents can temporally inhibit the proliferation of endometriotic tissues during the treatment by suppressing functions of a hypothalamo-pituitary-ovarian system and reducing an ovarian hormone. At the same time, the agents can make a menstrual pain disappear by inducing an amenorrheic state.

In the treatment by oral administration of danazol or by subcutaneous injection of GnRH analogs, the drugs circulate the entire body and therefore cause systemic side effects. Because of such side effects, in principle, administration for six months or more is prohibited. Further, these drugs do not directly act on the endometriosis cells themselves and there are many cases in which endometriosis recurs after the end of the treatment for six months. Specifically, if the administration is discontinued after the six-month period, secretion of the ovarian hormone starts again, and often, an endometriosis tissue grows due to the hormone's stimulation and the disease recurs.

As described above, the current therapeutic agents for endometriosis are not those which directly act on and cure endometriosis, and the agents only have an action of indirectly delaying temporally the development of endometriosis. Accordingly, it has been desired to develop a new therapeutic method of directly acting on the endometriotic tissues themselves and suppress systemic side effects to zero or a minimum. On the other hand, with respect to uterine adenomyosis, the above therapeutic agents for endometriosis are less effective, and there is now no effective conservative therapy except for total hysterectomy.

In such a circumstance, one of the present inventors has obtained a patent relating to a danazol topical administration preparation in which danazol is carried on a matrix base (Japanese Patent Laid-Open Publication No. 35335/1995 and Japanese Patent No. 2,590,358).

Meanwhile, 3-ethylpyridine has been used as an additive for many products such as food and cigarette. It has been reported that 3-ethylpyridine inhibits the growth of chorioallantoic membrane of chicken (Lin J. et al., Toxicological Sciences, Vol. 69, 217-225 (2002), and G. Melkonian et al., Anat. Embryol., Vol. 208, 109-120 (2004)). However, up to now, it has not been reported that 3-ethylpyridine is effective in treating and preventing of endometriosis or uterine adenomyosis.

DISCLOSURE OF THE INVENTION

The therapeutic agents for use in the treatment of endometriosis which are now commercially available and under development relate to medicaments that temporally suppress ovarian hormones, and do not have direct inhibitory act on endometriotic tissues. In particular, with respect to uterine adenomyosis, there has been reported no effective conservative therapy except for total hysterectomy. Furthermore, the therapeutic agents for the prevention of endometriosis and uterine adenomyosis have not been reported up to now.

An object of the present invention is to provide an effective therapeutic agent for use in the treatment and prevention of endometriosis and uterine adenomyosis.

The present inventors have found that the effective treatment of endometriosis and uterine adenomyosis can be achieved without systemic side effects by directly bringing 3-ethylpyridine into contact with the lesions of endometriosis and uterine adenomyosis through DDS (Drug Delivery System) technology.

Also, the present inventors have found that intractable severe cases of endometriosis can be more effectively treated by administering 3-ethylpyridine with danazol.

According to the present invention, there is provided an agent for use in the treatment and prevention of endometriosis or uterine adenomyosis, which comprises a compound selected from the group consisting of 3-ethylpyridine, 3-methylpyridine, 2-ethylpyridine, and 2-methylpyridine as an active ingredient.

Further, according to the present invention, there is provided use of a compound selected from the group consisting of 3-ethylpyridine, 3-methylpyridine, 2-ethylpyridine, and 2-methylpyridine, for the manufacture of a medicament for use in the treatment or prevention of endometriosis or uterine adenomyosis.

Further, according to the present invention, there is provided a method for treating and preventing endometriosis or uterine adenomyosis, comprising the step of administering, to a human for which the administration is indicated, a therapeutically or preventively effective amount of a compound selected from the group consisting of 3-ethylpyridine, 3-methylpyridine, 2-ethylpyridine, and 2-methylpyridine.

DETAILED DESCRIPTION OF THE INVENTION

The expression "endometriosis" in the present invention means a disease that a pathological lesion (namely, an endometriotic tissue) is recognized mainly in regions other than uterus in the pelvic cavity (for example, ovary, Cul-de-Sac (Douglas), and vagina). Specific examples of endometriosis include ovarian endometriosis (chocolate cyst), Cul-de-Sac endometriosis, vaginal endometriosis, deep endometriosis, or peritoneal endometriosis.

The expression "uterine adenomyosis" in the present invention means a disease that an endometrium-like tissue is recognized in a uterine wall, namely, uterine musculature.

In the therapeutic and preventive agents according to the present invention, an active ingredient such as 3-ethylpyridine can be combined and administered with other ingredients. The administration can be performed simultaneously or sequentially.

In the therapeutic and preventive agents according to the present invention, an active ingredient such as 3-ethylpyridine can be used in combination with danazol. As shown in Example 5, intractable severe cases of endometriosis and uterine adenomyosis can be more effectively treated by using an active ingredient such as 3-ethylpyridine in combination with danazol.

The effects of the therapeutic and preventive agents according to the present invention can be confirmed by performing a routine medical examination (for example, examination of change of menstrual bleeding amount and degree of pain), transvaginal ultrasonography, MRI inspection, and quantitative determination of CA125 and CA602 in the blood.

When pregnancy is confirmed during the treatment and prevention, side effects to an intrauterine baby can be avoided by immediately discontinuing the treatment and prevention.

The therapeutic and preventive agents according to the present invention can be administered to a human through an administration route (such as topical administration) suitable for the treatment and prevention of endometriosis and uterine adenomyosis. Specifically, the therapeutic and preventive agents according to the present invention can be formulated into a suitable preparation form for the administration route.

The topically administered agents suitable for the treatment and prevention of endometriosis and uterine adenomyosis include an intrauterine preparation (such as matrix preparation), an intravaginal preparation (such as a doughnut-shaped intravaginal ring), a vaginal pill, a vaginal suppository, a liquid preparation (such as injectable solution for topical), and so forth, but the present invention is not limited thereto.

Further, various preparations can be prepared by a conventional method using additives for preparation.

When the therapeutic and preventive agents according to the present invention are topically administered, the preparation form can be determined appropriately depending on the region having the lesion or the symptom of the patient. The respective preparation forms of the therapeutic and preventive agents according to the present invention will be specifically described below.

Intrauterine Preparation

According to the present invention, uterine adenomyosis can be treated and prevented by administering an intrauterine preparation containing an active ingredient such as 3-ethylpyridine to the cavity of the uterus. It is understood that 3-ethylpyridine permeates the adenomyosis tissue through a duct of the gland in the uterine endometrium and thereby the uterine adenomyosis is treated. In view of the continuous release of the active ingredient in the uterus, a matrix preparation having DDS effects is preferable as the intrauterine preparation.

In general, the insertion period of the intrauterine preparation can be about 6 months. When it is recognized that the disorder is cured, the preparation may be removed before the six-month period passes. When the disease state is improved but not fully cured after the 6 months, it is preferable that the preparation is exchanged to a new preparation so that the treatment is further continued.

The intrauterine preparation can be produced a general method using a matrix base (such as high polymer) and an inert intrauterine device. The intrauterine preparation is sufficient to have a suitable form for the topical administration in the uterus. The form is not particularly limited.

In the production of the matrix preparation, the inert intrauterine preparation may contain inside a matrix base. Such intrauterine devices include an inert intrauterine device to which silicon rubber is adhered.

The matrix base used in the production of the matrix preparation includes a polymer compound authorized for medical purposes, and includes, for example, a silicon rubber, ethylene vinyl acetate (Evatane), ethyl cellulose, carboxymethylethyl cellulose, polyethylene glycol, polyvinyl alcohol, carboxyvinyl polymer, or collagen. From the view of sustaining and releasing 3-ethylpyridine, a silicon rubber is preferable. Moreover, the matrix base may optionally contain a crosslinking agent, and the crosslinking agents used commonly depending on the type of the matrix base can be used.

A commercially available silicon rubber can be used and includes, for example, MDX 4-4210 (containing a crosslinking agent) (manufactured by Dow Corning Corporation) or Evatane (ethylene-vinyl acetate copolymer) (manufactured by ATOFINA Co., Ltd.).

In the matrix preparation, a release promoting agent can be optionally added. The available release promoting agent includes polysorbate 60, polysorbate 80, glycerin, isopropyl palmitate, and isopropyl myristate.

The matrix preparation may be a single-layered preparation, or a two-layered preparation including a core such as Silascon rod (measured by Dow Corning Corporation) or a contraceptive intrauterine device (such as FD-1) therein in view of enhancing hardness of the therapeutic agent.

The matrix single-layered preparation can be prepared by providing an active ingredient, a matrix base, and other optional ingredients in a container arranged in a clean bench, adding a curing catalyst, mixing them, and filling the mixture in a mold, followed by solidification.

For the matrix two-layered preparation, a desired core is embedded in the step of filling the resulting mixture in a mold during the steps of producing the above single-layered preparation, and then the mixture is solidified in the same manner, and thus the preparation can be produced.

In administering the therapeutic and preventive agents according to the present invention in the form of an intrauterine preparation, the dosage of 3-ethylpyridine and the like can be approximately from 0.1 to 5 mg per one preparation. However, it goes without saying that the present invention is not limited to the dosage.

When danazol is further added in the intrauterine administration agent according to the present invention, the dosage of danazol can be approximately from 80 to 500 mg per one preparation. However, it goes without saying that the present invention is not limited to the dosage.

Intravaginal Preparation

According to the present invention, endometriosis (in particular, deep endometriosis, Cul-de-Sac endometriosis, vaginal endometriosis, and peritoneal endometriosis) can be effectively treated and prevented by administrating an intravaginal preparation containing an active ingredient such as 3-ethylpyridine to the inside vagina of a patient. It is understood that the active ingredient is absorbed from the vaginal mucosa that is directly in contact with the intravaginal preparation, and the active ingredient permeates the deep endometriotic tissue existing in the rectovaginal septum, and thus the deep endometriosis or Cul-de-Sac endometriosis can be treated and prevented. In view of the continuous release of the active ingredient in the vagina, as the intravaginal preparation, an intravaginal ring such as a doughnut-shaped intravaginal ring is preferable.

Conventionally, the insertion period of the intravaginal preparation can be adjusted approximately from 1 to 3 months. When the disease state is improved but not fully cured after 1 to 3 months, it is preferable that the preparation is replaced by a new preparation so that the treatment is further continued.

The intravaginal preparation can be produced by a general method using a matrix base (such as high polymer) and inert devices (such as nuclear ring). The intravaginal preparation is sufficient to have a suitable form for the topical administration in the vagina, and the form is not particularly limited. The intravaginal preparation can be produced with reference to the method for producing an intrauterine.

In administering the therapeutic and preventive agents according to the present invention in a form of an intravaginal preparation, the dosage of 3-ethylpyridine can be adjusted approximately from 1 to 100 mg per one preparation. However, it goes without saying that the present invention is not limited to the dosage.

When danazol is further added in the intravaginal preparation according to the present invention, the dosage of danazol can be adjusted approximately from 50 to 4,000 mg per one preparation. However, it goes without saying that the present invention is not limited to the dosage.

Vaginal Pill and Vaginal Suppository

According to the present invention, endometriosis (in particular, deep endometriosis, Cul-de-Sac endometriosis, vaginal endometriosis, and peritoneal endometriosis) can be effectively treated and prevented by administrating a vaginal pill or a vaginal suppository containing an active ingredient such as 3-ethylpyridine to the inside of the vaginal. In the treatment or the prevention, for example, the preparation is deeply inserted into the vagina before bedtime.

The vaginal pill and the vaginal suppository can be produced by a common method using preparation additives such as a diluting agent, a binding agent, and a suppository base that are commonly used in the production of the preparations.

In administering the therapeutic and preventive agents according to the present invention in the form of vaginal pill and the vaginal suppository, the dosage of 3-ethylpyridine can be adjusted approximately from 10 μg to 5 mg per day. However, it goes without saying that the present invention is not limited to the dosage.

Moreover, when danazol is further added in the vaginal pill and the vaginal suppository according to the present invention, the dosage of danazol can be adjusted approximately from 10 to 100 mg per day. However, it goes without saying that the present invention is not limited to the dosage.

Liquid Preparation

According to the present invention, endometriosis (in particular, ovarian endometriosis cyst (chocolate cyst), deep endometriosis, Cul-de-Sac endometriosis, and peritoneal endometriosis) can be effectively treated and prevented by administrating a liquid preparation containing an active ingredient such as 3-ethylpyridine to the inside of the vagina.

In the treatment, the liquid preparation according to the present invention is injected into a diseased area through the vagina or under a laparoscopy and the active ingredient is made to directly permeate the endometriotic tissue and thereby, the endometriosis can be treated. When a cyst is formed in the diseased area, it is preferable to aspirate the content of the cyst before the injection of the liquid preparation. In the prevention, the preparation can be injected into an area in which endometriosis is anticipated to generate.

Specifically, for the cyst contiguous (for example, within about 1 cm) to posterior vaginal fornix, under a transvaginal ultrasonic guide, the content of the cyst is aspirated and removed by puncturing from the posterior vaginal fornix and then, the preparation can be injected into the area. For the cyst separate from the posterior vaginal fornix, under a laparoscopy, the content of the cyst is aspirated and removed by puncture and then, the preparation can be injected into the site.

The solvent used for preparing the liquid preparation can be selected from biocompatible solvents, and the solvent that is slowly absorbed to the body is desirable. Such solvents include a poppy oil, a lipiodol oily solution, a diluted ethyl alcohol solution, and an ethyl ether solution. However, the present invention is not limited thereto.

The dosage of 3-ethylpyridine or the like in the therapeutic and preventive agents according to the present invention can be adjusted approximately from 100 μg to 10 mg per once. However, it goes without saying that the present invention is not limited to the dosage.

Moreover, when danazol is further added in the liquid preparation according to the present invention, the dosage of danazol can be adjusted approximately from 5.0 to 100 mg per once. However, it goes without saying that the present invention is not limited to the dosage.

In the administration of the liquid preparation, the preparation containing 3-ethylpyridine or the like and danazol may be separately prepared and administered simultaneously or sequentially.

EXAMPLES

The present invention will now be described in detail by way of Examples, but the present invention is not limited to the following Examples.

Example 1

Therapy of Uterine Adenomyosis (1)

A patient (35 years old) having uterine adenomyosis was subjected to the treatment using the therapeutic agent according to the present invention. The patient had been subjected to injection of Leuplin, which was a therapeutic drug for endometriosis at one time per a month continuously for six months. However, the disease was not cured. Then, the uterus was enlarged to have a size corresponding to the third month of pregnancy, and menstrual pain was severe, and a menstrual bleeding was abundant. Moreover, CA125 in the blood indicated 441 units (the normal units are 35 units or less) and CA602 indicated 1025 units (the normal value is 63 units or less). The indicated values were abnormally high.

Accordingly, an IUD-type device containing 825 μg of 3-ethylpyridine was inserted into the uterus, and as a result, the size of the uterine corpus was scaled down to a normal size six months after the insertion. The menstrual pain and the hypermenorrhea disappeared. Moreover, CA125 in the blood was reduced to be 38 units and CA602 was reduced to 53 units after 60 days from the initiation of the administration. Accordingly, it can be said that the uterine adenomyosis was fully cured. After suspension of the treatment by the present invention, the recurrence was not recognized.

Example 2

Therapy of Uterine Adenomyosis (2)

An intrauterine device (IUD) containing 600 μg to 900 μg of 3-ethylpyridine was inserted for 6 months into the vagina of each of patients (12 cases) having uterine adenomyosis recurring after the nasal administration or injection of GnRH analogs. As a result, in nine cases, the hypermenorrhea disappeared, and in three cases, improved. In eight cases, menstrual pain disappeared, and in four cases, improved. Therefore, in all the cases, therapeutic effect was recognized. On the other hand, the dropout rate of IUDs in menstruation was 20%, which was a high ratio.

An intrauterine device (IUD) containing 600 to 900 μg of 3-ethylpyridine and 300 to 400 mg of danazol was inserted for 6 to 12 months into the vagina of each of patients (55 cases) for whom hypermenorrhea and menstrual pain are considerably improved by the treatment with IUDs containing danazol, but the uterine adenomyosis was not cured, out of patients having uterine adenomyosis recurring after the nasal administration or injection of GnRH analogs. As a result, in 49 cases, the hypermenorrhea disappeared, and in 6 cases, improved. In 45 cases, menstrual pain disappeared, and in 9 cases, improved. Therefore, the more excellent effects than the cases of IUDs singly containing danazol were recognized. The dropout rate of IUDs in menstruation was 12.0%, which was more improved than the group of IUDs singly containing 3-ethylpyridine.

Example 3

Therapy of Vaginal Endometriosis

A patient (33 years old) having endometriosis recurred after operation of the left ovary and Cul-de-Sac endometriosis was subjected to the treatment using the therapeutic agent according to the present invention. In the patient with an induration about 7 cm×about 5 cm in a deep right posterior fornix of the vagina. The induration was demonstrated to be a vaginal endometriosis by biopsy. Moreover, menstrual pain, extramenstrual pain, severe lower abdominal pain, defecation pain, and coital pain were recognized.

Accordingly, the above-described doughnut-type ring containing 9 mg 3-ethylpyridine was inserted into the posterior vaginal fornix. As a result, four weeks after the insertion, the coital pain, the defecation pain, the extramenstrual lower abdominal pain and low back pain disappeared, and the menstrual pain was reduced. The induration at the right posterior fornix of the vagina was scaled down to 4 cm×2 cm. Then, by continuous treatment, the induration at the right posterior fornix of the vagina was further scaled down to have 2 cm×1 cm.

In addition to the above case, with respect to each of patients of other two cases having endometriosis, the pathological endometriosis was confirmed by biopsy and then, a vaginal ring containing 8 to 10 mg of 3-ethylpyridine was inserted into the vagina. As a result, the vaginal endometriosis disappeared macroscopically and histologically in all two cases. At the same time, the menstrual pain and the defecation pain that were recognized before the treatment disappeared in all the cases.

Example 4

Therapy of Ovarian Chocolate Cyst

A patient having ovarian chocolate cyst was subjected to the treatment using the therapeutic agent according to the present invention. In this patient, by transvaginal ultrasonic diagnosis, the cyst having a diameter of 6 cm was recognized in Cul-de-Sac. Moreover, CA125 in the blood indicated 1522 units and CA602 indicated 352 units (the normal value is 63 units or less). The indicated values were abnormally high. It was confirmed that the distance from the vaginal fornix to cyst was within 1 cm, and under observation with a transvaginal ultrasonography, the cyst content was punctured with a needle from the posterior vaginal fornix and was aspirated. Then, the 2 mL ethanol solution containing 2 mg of 3-ethyl pyridine was injected. As a result, the ovarian chocolate cyst disappeared four weeks after the injection. The uterus was scaled down to 2.5 cm. The menstrual pain disappeared. Moreover, CA125 in the blood was lowered to be 52 units and CA602 was lowered to be 61 units.

In addition to the above case, patients of other 12 cases having chocolate cysts were subjected to the following treatment. That is, under a transvaginal ultrasonic guide, the ovarian chocolate cyst having a distance within 10 mm from the posterior vaginal fornix was punctured and the cyst content was aspirated and then the 3 mL ethyl ether solution containing 3 mg of 3-ethylpyridine was injected into the cyst. As a result, in all 12 cases, the ovarian chocolate cyst was scaled down, and at the same time, the menstrual pain disappeared in eight cases, and, improved in three cases. The cyst of each of the three cases that was enlarged again after the six months was punctured as above-described and subsequently, the 3-ethylpyridine solution was injected thereto, and the ovary chocolate cyst could be cured. In addition, existence of malignant cells in the aspirated cystic content was denied by cyto-diagnosis.

Example 5

Therapy of Deep Endometriosis (1)

A patient (34 years old) suffered from intensive menstrual pain by deep endometriosis was subjected to the treatment using the therapeutic agent according to the present invention. First, a vaginal ring containing 1,000 mg of danazol was inserted into the vaginal for 6 months and then, CA125 in the blood decreased from 950 units to 620 units, and the menstrual pain was reduced but not fully cured. Also, painful induration in Cul-de-Sac was not scaled down. Next, a vaginal ring containing 10 mg of 3-ethylpyridine was inserted and then, CA125 became 250 units in 3 months, and the menstrual pain further decreased. However, the induration in Cul-de-Sac was not scaled down. Accordingly, a vaginal ring containing 1,000 mg of danazol and 10 mg of 3-ethylpyridine was inserted and then, the menstrual pain disappeared in 2 months. Moreover, it became impossible to palpate the painful induration in Cul-de-Sac, and CA125 decreased to a normal value. The deep endometriosis was fully cured.

Example 6

Therapy of Deep Endometriosis (2)

A vaginal ring containing 8 to 10 mg of 3-ethylpyridine was inserted into the vagina of each of deep endometriosis patients (18 cases) for 3 months. As a result, disappearance of pressure pain and induration in Cul-de-Sac was recognized in 9 cases, and improvement thereof was recognized in 7 cases, and nullity thereof was recognized in 2 cases. The menstrual pain disappeared in 4 cases, and improved in 13 cases and null in only one case. A coital pain disappeared in 10 cases and a defecation pain was improved in 7 cases.

The invention claimed is:

1. A method for treating endometriosis or uterine adenomyosis, comprising the step of administering, to a human, a therapeutically effective amount of a compound selected from the group consisting of 3-ethylpyridine, 3-methylpyridine, 2-ethylpyridine, and 2-methylpyridine.

2. The method according to claim 1, wherein a therapeutically effective amount of danazol is administered simultaneously or sequentially.

3. The method according to claim 1, wherein the endometriosis is ovarian endometriosis (chocolate cyst), Cul-de-Sac endometriosis, vaginal endometriosis, deep endometriosis, or peritoneal endometriosis.

4. The method according to claim 1, wherein the compound is topically administered.

5. The method according to claim 4, wherein the compound is administered in the form of a topical administration agent selected from the group consisting of an intrauterine preparation, an intravaginal preparation, a vaginal pill, a vaginal suppository, and a liquid preparation.

6. The method according to claim 1, wherein the compound is injected into a diseased area.

7. The method according to claim 6, wherein the compound is administered in the form of a liquid preparation.

8. The method according to claim 6 or 7, wherein the diseased area is an endometriotic tissue in ovary, Cul-de-Sac (Douglas), vagina, or uterine musculature.

9. The method according to claim 1, wherein the compound is 3-ethylpyridine.

* * * * *